(12) United States Patent
Raina et al.

(10) Patent No.: US 7,790,151 B1
(45) Date of Patent: Sep. 7, 2010

(54) **STRAIN OF THE FUNGUS *METARHIZIUM ANISOPLIAE* FOR CONTROLLING SUBTERRANEAN TERMITES**

(75) Inventors: Ashok K. Raina, New Orleans, LA (US); Maureen S. Wright, New Orleans, LA (US); Alan R. Lax, Poplarville, MS (US)

(73) Assignee: The United States of America as represented by the Secretary of the Agriculture, Washington, DC (US)

( * ) Notice: Subject to any disclaimer, the term of this patent is extended or adjusted under 35 U.S.C. 154(b) by 1072 days.

(21) Appl. No.: 11/389,609

(22) Filed: Mar. 24, 2006

(51) Int. Cl.
*A01N 25/00* (2006.01)
*C12N 1/00* (2006.01)
(52) U.S. Cl. .................. 424/84; 424/93.5; 435/254.1
(58) Field of Classification Search .................. None
See application file for complete search history.

(56) References Cited

U.S. PATENT DOCUMENTS 6,660,290 B1 * 12/2003 Stamets ...................... 424/406
2004/0170661 A1 * 9/2004 Brode et al. ................ 424/410

OTHER PUBLICATIONS

Dean, P., et al., "Modulation by Eicosanoid Biosynthesis Inhibitors of Immune Responses by the Insect *Manduca sexta* to the Pathogenic Fungus *Metarhizium anisopliae*", *J. Invertebrate Pathology*, vol. 79, pp. 93-101, 2002.

Sun, J., et al., "Effects of Virulence, Sporulation, and Temperature on *Metarhizium anisopliae* and *Beauveria bassiana* Laboratory Transmision in *Coptotermes formosanus*", *J. Invertebrate Pathology*, vol. 84, pp. 38-46, 2002.

Sun, J. et al., "Sporulation of *Metarhizium anisopliae* and *Beauveria bassiana* on *Coptotermes formosanus* and in vitro", *J. Invertebrate Pathology* vol. 81, pp. 78-85, 2003.

* cited by examiner

*Primary Examiner*—Shanon A Foley
(74) *Attorney, Agent, or Firm*—John D. Fado; Evelyn M. Rabin (57) ABSTRACT

Alates of the Formosan subterranean termite (FST), *Coptotermes formosanus* Shiraki, collected after swarming in 2002 died within 48 hrs, and the cadavers were visibly infected with a fungus. Fungi were picked from the cadavers, transferred to media and ultimately isolated to purity. A single fungal isolate, C4-B, taxonomically identified as *Metarhizium anisopliae* (Metschnikoff), was found to cause rapid mortality of FST alates. This is the first report of a biological control agent for termite alates. Strain C4-B was more lethal to both alates and workers when compared to *M. anisopliae* strain ESC1, marketed as the termite biocontrol agent Bio-Blast®. 100% of FST alates exposed to C4-B spores ($10^6$ spores/$\mu$l) were killed in 3 days. Field studies where C4-B spores were dispersed on grassy lawns resulted in 100% mortality of alates by day 5.

23 Claims, 5 Drawing Sheets

STRAIN OF THE FUNGUS *METARHIZIUM ANISOPLIAE* FOR CONTROLLING SUBTERRANEAN TERMITES

BACKGROUND OF THE INVENTION

1. Field of the Invention

This invention relates a new strain of the fungus *Metarhizium anisopliae*, compositions thereof, and methods of using the compositions for control of Formosan and other subterranean termites, in particular their alate stage.

2. Description of the Relevant Art

Subterranean termites, including the Formosan subterranean termite (FST), *Coptotermes formosanus* Shiraki, cause an estimated one billion dollars in prevention and control costs in the United States annually (Potter, M. 1997. In: *Handbook of Pest Control*, Moreland, D. (Ed.), Mallis G. I. E. Publishing, Cleveland, Ohio, pp. 232-332). The FST is becoming the predominant termite pest species in several southern states and Hawaii. Current FST control methods involve slow-acting, non-repellent termiticides and baits (Su and Scheffrahn. 1998. *Integrated Pest Mangt. Rev.* 3: 1-13). Insect pathogens are attractive candidates for baiting because of their self-replicating nature and safety to non-target animals. According to Glare and Milner (1991. In: *Handbook of Applied Mycology, Vol. 2, Humans, Animals, and Insects*, Arora et al. (Eds.), Marcel Dekker Inc., New York, pp. 547-612), the most virulent isolates are those derived from the target insect infected under natural field conditions. Factors that have limited the development of termite biological control agents include: (1) removal of the pathogen by termites by grooming, and (2) isolation of infested members of the colony (Culliney and Grace. 2000. *Bull. Entomol. Res.* 90: 9-21).

Most studies addressing the conditions required for control of subterranean termites in the field have focused on *Metarhizium* spp. and *Beauveria* spp. (Milner et al. 1998b. *Australia. Biol. Control* 11: 240-247, Sun et al. 2002. *J. Invertebr. Pathol.* 81: 78-85, Sun et al. 2003a. *J. Inverteb. Pathol.* 84: 38-46). In addition, Wright et al. (2003. U.S. Pat. No. 6,660, 291) have recently patented *Paecilomyces* spp. for controlling subterranean termites. These *Paecilomyces* strains are non-repellent, are transferred among termites and cause rapid mortality of termite workers. In the studies of Milner et al. in Australia (1998b, supra), 93 isolates of *Metarhizium anisopliae*(Metschnikoff), obtained from two species of termites, were tested. Isolate FI-610 was found to be one of the most effective. Successful control of *Coptotermes acinaciformis* (Froggot) was achieved using direct inoculation with $3 \times 10^{11}$ conidia into termite mounds. While it can be difficult to identify the location of an FST nest within a structure, infestations in trees are similar to termite mounds in that they allow localized access, similar to Milner et al., for direct treatment. In addition, biological control agents found to be effective for termite population management can be used alone (Grace, J. K. 2003. *Sociobiol.* 41: 115-121) or in a synergistic partnership with chemical termiticides (Boucias et al. 1996. *Pflanzenschutz-Natrichten Bayer* 49: 103-143).

*Metarhizium anisopliae*(*M. anisopliae*) is a well known fungal pathogen of a wide range of insect species (Hanel and Watson. 1983. *Bull. Ent. Res.* 73: 305-313; Rath et al. 1995. *Biocontrol Sci. Technol.* 5: 439-451; Jones et al. 1996. *Environ. Entomol.* 25: 481-487; Milner et al. 1998b, supra; Ramakrishnan et al., 1999. *J. Econ. Entomol.* 92: 1125-1132; Staples and Milner. 2000. *Sociobiol.* 36: 133-148; Dean et al. 2002. *J. Invert. Pathol.* 79: 93-101) and, as discussed above, has been used in the control of subterranean termites. An isolate of this fungus, ESC 1, has been commercialized as a mycoinsecticide (BioBlast®) for use in termite control. However, it does not cause high mortality among both FST workers and alates, as shown in the studies of the invention. When allowed to infect FST alates, strain ESC 1 caused only moderate rates of mortality over relatively long periods of time.

Thus there remains a need to obtain effective additional agents for controlling FST alates. Herein we report the isolation of a strain of *M. anisopliae*, strain C4-B. The C4-B strain causes rapid mortality among both FST alates and FST workers and is thus an effective agent for controlling subterranean termites.

SUMMARY OF THE INVENTION

We have isolated a strain of *Metarhizium anisopliae*, designated strain C4-B, and discovered that this *M. anisopliae* strain C4-B causes rapid mortality among both alates and workers of subterranean termites, particularly, Formosan subterranean termites (FST), and is therefore useful for the control of termite infestations.

In accordance with this discovery, it is an object of the invention to provide the isolated *M. anisopliae* strain C4-B which can act as a biocontrol agent and cause rapid mortality of Formosan and other subterranean termite alates and workers. In the preferred embodiment of the invention, the strain designated as C4-B and variants thereof are provided.

It is a further object of the invention to provide a biocontrol composition for increasing mortality of subterranean termite alates and workers, particularly FST, wherein said composition comprises the *M. anisopliae* strain C4-B as a biocontrol agent.

It is another object of the invention to control termite infestation with a biocontrol formulation composed of an effective dose of *M. anisopliae* strain C4-B in a suitable carrier for delivery to the Formosan and other subterranean termites as a biocontrol agent.

It is yet another object of the invention to provide a method for the biocontrol of the Formosan and other subterranean termite alates and workers.

It is an additional object of the invention to provide a biocontrol method for increasing the mortality rate of the Formosan and other subterranean termite alates and workers which includes applying the *M. anisopliae* strain C4-B in, on, or near a currently or potentially infested area, structure or tree as a biocontrol agent to control FST alates and workers.

It is an added object of the invention to provide a component of termite treatment strategies and formulations that will enhance the control of and reduce damage by termites. The control and suppression of termite colonies is effective when an integrated pest management strategy is utilized. The biocontrol agent *M. anisopliae* strain C4-B is one component of the strategy to control FST alates and workers.

Also part of this invention is a kit, comprising a biocontrol composition for application in, on, or near a currently or potentially infested area, structure or tree, to increase mortality of FST alates and workers.

Other objects and advantages of this invention will become readily apparent from the ensuing description.

DETAILED DESCRIPTION OF THE INVENTION

It has been proposed that the natural presence in the soil of pathogenic fungi particularly *Metarhizium* and *Beauveria*, may contribute to control of FST by killing termites before new colonies can be established (Sun et al. 2003a, supra; Sun et al., 2003b. *J. Entomol. Sci.* 39(3): 342-358). Other studies have shown that while termite nests are generally free of fungal disease (Milner, R. J. 1997. In: *Soil Invertebrates*, Allsopp et al., (Eds.), Bureau of Sugar Experiment Station, Brisbane Paddington, Australia, pp. 63-67; Milner et al. 1998a. *Mycol. Res.* 102: 216-220; Roberts and Humber. 1981. In: *Biology of Conidial Fungi*, Vol. 2, Cole et al. (Eds.), Academic Press, New York, pp. 201-236), the success of founding pairs in new soil is low (Fei, H. X. 2000. Comparative Biology and Ecology of the Formosan subterranean termite, *Coptotermes formosanus* Shiraki (*Isoptera: Rhinotermitidae*) in Louisiana. Ph. D. Dissertation. Louisiana State University, Baton Rouge, La.; McMahan, E. 1962. *Proc. Hawaii Entomol. Soc.* 18: 145-153; Rosengaus and Traniello. 1993. Proc. Natl. Acad. Sci. USA 90: 6641-6645). Because alates give rise to new colonies after swarming, elimination of this caste through targeted delivery of a pathogenic fungus before or during a swarm could be crucial to long-term termite management.

Figure 1:
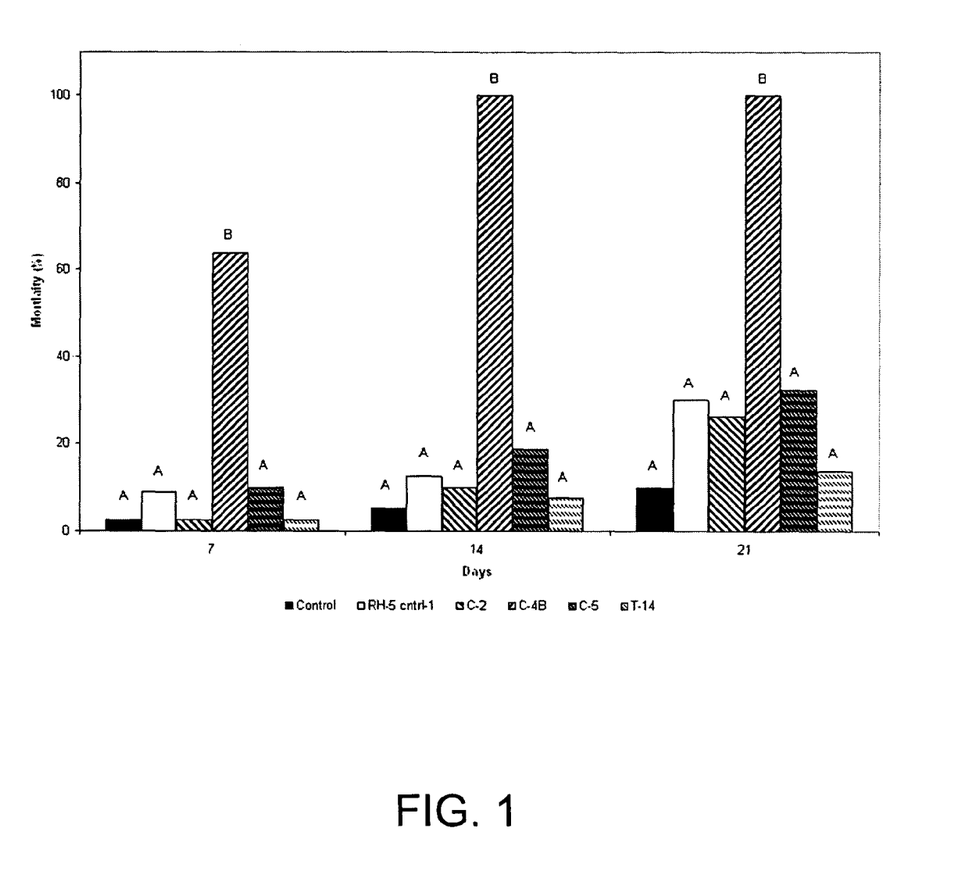
FIG. 1 depicts the percent mortality of FST workers following exposure to fungal strains newly isolated from FST alate cadavers.

A group of FST alates collected in a light trap in New Orleans during the 2002, swarming season showed unusually high, rapid mortality and were quickly covered with fungal mycelia and conidia. Several fungal strains isolated from the alate cadavers were purified individually. Each purified strain was first tested for mortality effects against FST workers because the newly isolated strains could not immediately be tested on alates, as the alate season had ended by the time the fungal strains were purified. Of the five strains tested, only one strain, designated C4-B, caused significant mortality among workers. C4-B caused 63.8% mortality by day 7 and all of the termites were dead by day 14 (FIG. 1). C4-B was identified as a strain of *M. anisopliae*; the other four strains were not *M. anisopliae*.

Figure 2:
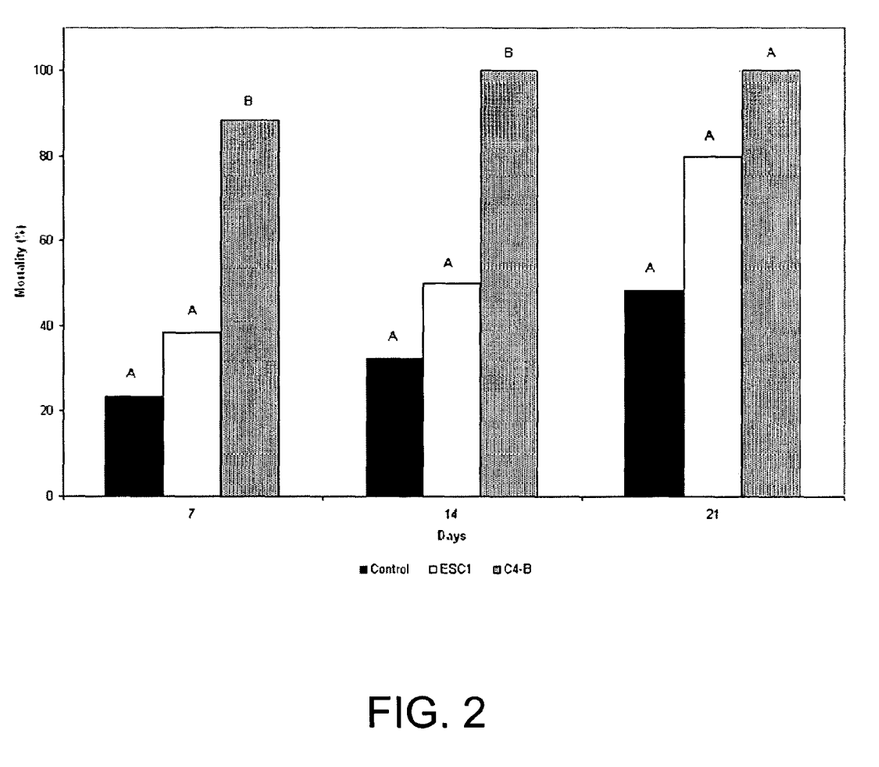
FIG. 2 depicts the percent mortality of FST workers following exposure to a commercial strain (ESC 1) and a newly isolated strain (C4-B) of *M. anisopliae*.

The effectiveness of the *M. anisopliae* C4-B strain was further evaluated in 2003 by exposing FST workers to either ESC 1, a strain of *M. anisopliae* produced commercially for control of termites under the product name BioBlast®, or the newly identified strain C4-B. Whereas 100% of the workers in the C4-B-treated group were dead after 14 days, thus repeating the effective results observed previously in 2002, only 50% of the termites treated with ESC 1 died during that same period (FIG. 2). To test efficiency of strain C4-B against alates, a dilution series of fungal spores in silica was applied to freshly collected alates. An undiluted dose of C4-B killed 100% of the exposed alates in three days; administration of doses diluted 1:10 and 1:100 reached maximal mortality rates of 95.8% and 20.6% mortality by day 4, respectively. By comparison, an undiluted preparation of strain ESC 1 caused a mortality rate of only 73.3% among alates after four days.

Because of the role of infected termites transporting fungal spores into the nest, the mortality of FST workers was examined under conditions where different proportions of termites were exposed to strain C4-B and incubated with uninfected nestmates. After 21 days, 1:19, 1:9 and 1:4 ratios of infected to uninfected individuals caused mortality rates of 35.0%, 43.3% and 62.8%, respectively, compared to a control mortality rate of 14.5%. Transmission of the C4-β isolate to other untreated nestmates is evident by the mortality, within 21 days, of greater numbers of workers than were originally exposed to spores of the fungus. Thus, even though only 5% of the workers were originally inoculated, 35% of the total population was killed by day 21. Transfer of a pathogen among individual termites of a population, particularly in the case of subterranean termites, is necessary for a fungus to work successfully as a biocontrol agent in the field.

Figure 3:
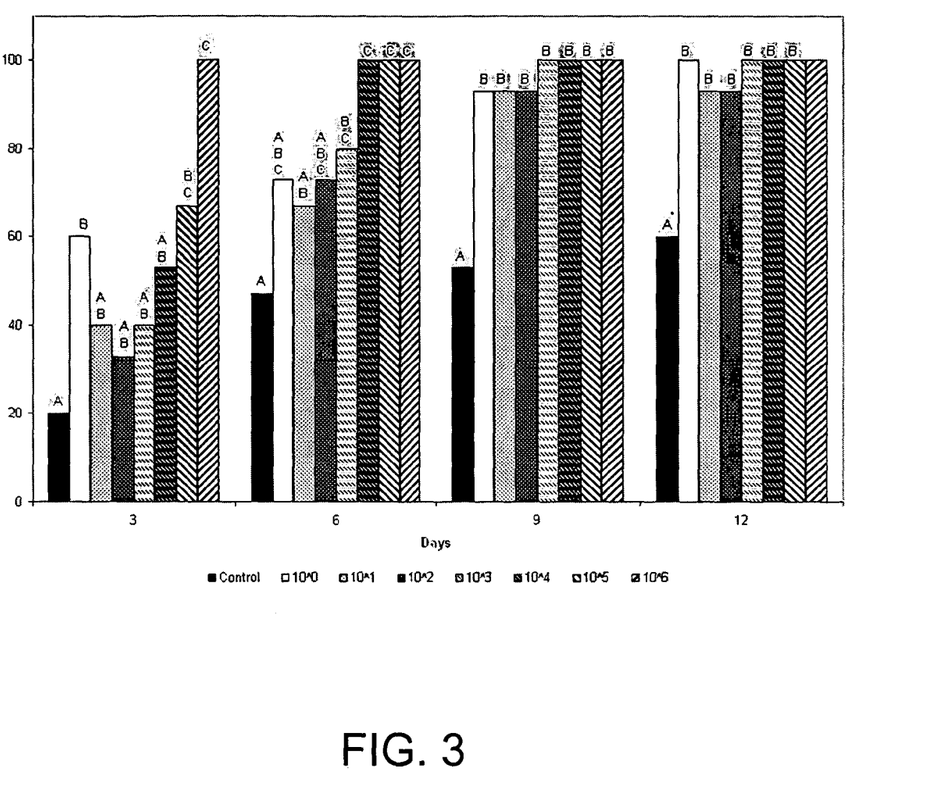
FIG. 3 shows the dose response of FST alates to known spore concentrations of *M. anisopliae* strain C4-B.

To determine the number of spores required to kill a single termite, dose response experiments were designed as a measure of mortality from a known inoculum. Alates immobilized on ice received a single ventral application of C4-B ranging from $10^0$ through $10^6$ spores/µl. All alates exposed to a concentration of $10^6$ spores/µl were dead by three days after exposure, those exposed to $10^5$ and $10^4$ spores/µl, by six days, and those exposed to $10^3$ spores/µl, by nine days (FIG. 3). By the ninth day, treatments with $10^3$, $10^2$, $10^1$ and $10^0$ spores/µl had all reached a mortality rate of 93.3% (FIG. 3). The control mortality rate on day 9 was 53.3%.

Figure 4:
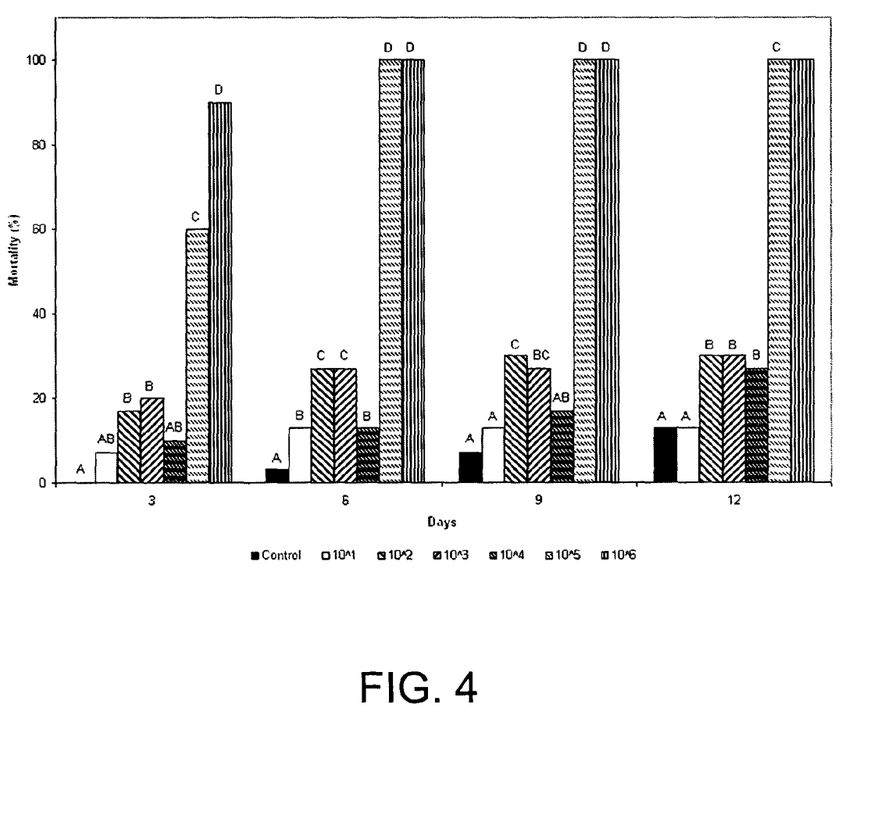
FIG. 4 shows the dose response of FST workers to known spore concentrations of *M. anisopliae* strain C4-B.

Dose response was also measured with FST workers. Workers exposed to $10^6$ and $10^5$ spores/µl reached 100% mortality by day 6 (FIG. 4). No other treatment reached 100% mortality. The mortality in the control group was only 3.3% after six days. Mortality caused by dilutions ranging from $10^4$ and $10^1$ spores/pl did not exceed 30% by day 12 of the experimental period.

Figure 5:
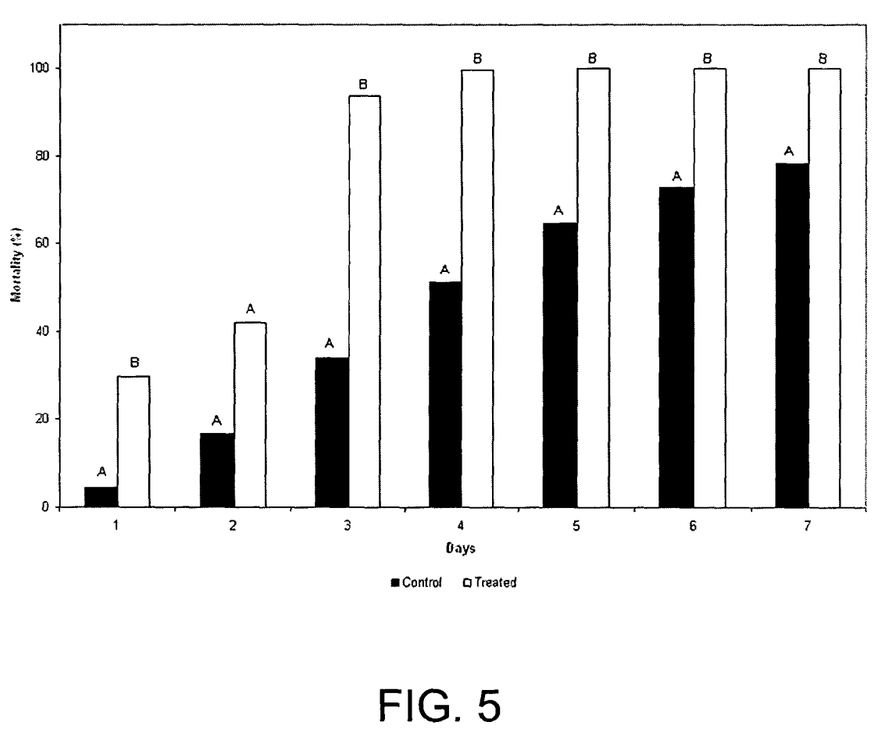
FIG. 5 depicts the percent mortality of FST alates following exposure to spores of *M. anisopliae* strain C4-B in the field.

Field trials were performed to measure the effectiveness of strain C4-B against field exposed alates. At each test site swarming alates were attracted to black lights placed at the center of grassy areas inoculated either with C4-B spores mixed with corn cob grits, or corn cob grits alone (control). Mortality of alates collected from the treated area reached 93.6% in three days; mortality of the untreated alates was only 34.0% for the same period (FIG. 5). Moreover, exposed alates showed 100% mortality in six days, while alates not exposed to the fungus showed a maximum of only 64.8% mortality on day 6 (FIG. 5). Groups of alates kept in Petri dishes do not generally survive longer than seven to eight days (data not shown).

Fungi were recovered from FST cadavers following field tests by plating the cadavers in PDA and serially purifying fungi that grew from them. Alcohol washing was used to remove and/or kill fungal spores on the surface of the termite to allow growth of fungi inside the cadaver. Recovery yielded more fungi from termites exposed to C4-B (78% from washed and 63% from unwashed cadavers) than controls (22% from washed and 37% from unwashed cadavers). Fungal cultures presumed to be *Metarhizium* sp. by morphological comparison to a representative sample were more evenly distributed; 45% were recovered from washed C4-B-exposed cadavers, 23%, from unwashed C4-B-exposed cadavers, 25%, from washed control and 26%, from unwashed control cadavers (data not shown). It is not unusual to find *Metarhizium* spores on the surface of termites from natural exposure to the fungus in the soil. Further genetic analysis would be necessary to determine if the newly isolated virulent strain described here is the strain present in each of the cadavers. These data show that the majority of the fungi were recovered from the termites known to have been exposed to C4-B.

Alates stay in a parent colony for one week to two weeks prior to swarming. Strain C4-B is easy to grow on available media and its spores, when mixed with an inert carrier, can be introduced into termite nests as a powder to infect the maturing alates. Alternatively, spores could be broadcast to infect alates during their dispersal flights. Additionally, the spores will also kill workers, thereby reducing the overall colony population. High relative humidity inside a subterranean termite colony and a confined area are considered conducive to the growth and survival of pathogenic agents such as fungi (Ignoffo, C. 1992. Florida Entomol. 75: 516-525). Existing control measures are directed primarily against FST workers. Strain C4-B, while rapidly killing alates, is also lethal to workers. This strain has the potential to be produced in large quantity and formulated for control of termites in an integrated pest management system.

For purposes of this invention, a fungal preparation or fungal agricultural biocontrol composition refers to a microbial preparation wherein the microbes comprise, consist essentially of, or consist of *M. anisopliae* strain C4-B. The fungal preparations may contain one or more strains of *M. anisopliae*. The agricultural biocontrol composition for purposes of this invention includes a strain or strains of fungi on agriculturally acceptable carriers which may be any carrier to which the fungi can be attached and are not harmful to the fungi or surfaces which are treated with the composition. The fungi especially useful in the present invention are strains possessing the identifying characteristics of *M. anisopliae* strain C4-B (SRRC 2571), designated NRRL 30905. An identifying characteristic includes the attribute that treatment with such a *M. anisopliae* fungal isolate is effective for inducing significant mortality of both subterranean termite alates as well as workers when applied to nests or populations of alates and/or workers.

As used herein, the term "termiticide" refers to a material or mixture of materials which induce mortality, disrupt or impede growth, interfere with metamorphosis or other morphogenic functions, effect sterilization, or interfere with reproduction of the targeted termites. The term "controlling" is used herein to mean that the population is reduced, principally through mortality, at a level that is significantly greater than an untreated population. As used herein "increase mortality" refers to an increase in the numbers of deaths compared to that which would be expected in populations which were not treated according to the methods of the present invention. Any accurate method of measuring and comparing mortality may be used for such comparisons, as would be apparent to those skilled in the art. "Significant mortality" is defined herein to mean that the percentage of insects that die within a given period of time after coming into contact with the termiticide is significantly greater than the number of insects not contacted with the termiticides that die during the same period of time. An "effective amount" is used herein in reference to that quantity of biocontrol agent necessary to obtain significant mortality in a population or colony of termites. The actual rate amount of agent needed for a particular application will be dependent upon a number of factors, such as the mode of application, the environmental conditions, the particular fungal strain being used, the species of target termite, and the composition of the formulation. The person of ordinary skill in the art would be able to experimentally determine an actual effective amount for a particular situation by observing the success of a control regimen, and then modifying it accordingly.

*M. anisopliae* strain C4-B is cultured as a single strain on medium, such as PDA. These cultures contain approximately $10^6$ colony forming units (CFU) of fungi per plate. The cultured product is stored at about 5° C. until use.

Infection of termites with *M. anisopliae* strain C4-B is effected by application of a control agent comprising fungal propagules directly to termites, to the locus of termites, to material susceptible to termite infestation, or to the locus of material susceptible to termite infestation. Treatment areas may include woody environments such as lumber, structures or buildings constructed at least in part from wood, dead or living plants, particularly trees, forests, orchards or other agricultural fields which are subject to termite attack. The soil surface around the plant provides a humid, protected environment which promotes growth and sporulation of the fungus.

The data presented herein were generated through the use of fungal cultures scraped from plates. Additional propagules of interest are spores (i.e. blastospores), and particularly dessication tolerant blastospores as described by Jackson in U.S. Pat. No. 5,968,808, herein incorporated by reference. The blastospores described by Jackson are produced in a liquid culture medium. Also contemplated by the invention are control agents comprising primarily *M. anisopliae* strain C4-B blastospores in combination with *M. anisopliae* strain C4-B conidia and/or mycelia. These may be applied to the treatment area in the form of a recovered culture broth or in combination with a suitable vehicle or carrier that does not substantially interfere with the viability of the fungus. The *M. anisopliae* strain of the invention, strain C4-B, may be delivered using methods similar to those employed by Milner et al. (1998b, supra).

Subterranean termites are normally attracted to and reliant upon the presence of moisture; therefore, water is a particularly preferred carrier, although other carriers suitable for use herein include but are not limited to alcohols, ethers, glycols, ketones, esters, and solid carriers such as clays, silicas, cellulosics, rubber, or synthetic polymers. It may also be desirable to incorporate a humectant, such as methylcellulose or polyacrylamide, to maintain the moisture content in the composition. The *M. anisopliae* strain C4-B -containing pesticidal compositions of this invention may, for example, be formulated as wettable powders, dusts, granules, baits, solutions, emulsifiable concentrates, emulsions, suspension concentrates and sprays (aerosols).

The fungal biocontrol agents of the invention may be applied to, or impregnated into, a bait matrix intended to be placed in bait stations. The matrices that have potential for use in bait stations in accordance with the invention would include solids, semi-solids, or liquids. The bait stations are usually placed at least partially below the soil surface, but may also be completely above ground. It has been found that placement of a bait station in the path of an active mud tube is effective for achieving contact of the bait matrix by the termites. When the station is in the vicinity of a termite colony, termites will preferentially feed on the treated bait, and thereafter transfer the biocontrol agent to other members of the colony. The matrix will usually contain a form of cellulose as an attractant. Suitable cellulose-containing materials for use as bait matrices include, but are not limited to paper, paper products (e.g., virgin paper, recycled paper, or a combination of both), cotton linter, cardboard, paperboard, wood, sawdust, wood particles or wood flour, processed or purified cellulose, cellulose derivatives such as cellulose ethers, and including, for example, methylcellulose, hydroxypropylmethylcellulose, and hydroxybutylmethylcellulose, or other agricultural fibers. Bait matrices may also contain other organic materials that provide nutrition, attractant or arrestant properties, such as those described by Rojas et al. (U.S. Pat. No. 6,585,991, issued Jul. 1, 2003).

The *M. anisopliae* strain C4-B biocontrol agent described above may be used alone or in combination with other (secondary) termiticides. Suitable secondary termiticides include, but are not limited to, biological and biorational control agents such as pathogenic nematodes, other fungi, protozoans, or bacteria, growth and developmental hormones and toxicants. The mortality rate of the faster-acting termiticide of the invention may be retarded by microencapsulation or other slow-release formulation. Biological control agents that may be used as secondary termiticides include fungi such as *Aspergillus flavus* and *Beauveria bassiania*, nematodes such as *Neoplectana carpocapsae*, insect viruses, pathogenic bacteria such as *Bacillus thuringiensis* and *Serratia marcescens*, and toxins derived from biological control agents such as the above bacteria and fungi. The mortality rate of the faster-acting termiticide of the invention may be retarded by microencapsulation or other slow-release formulation.

Optionally, the *M. anisopliae* strain C4-B -containing compositions may be further formulated with other insect attractants such as pheromones of the target termites or termite extracts containing pheromones or pheromone mimics. Termite pheromones suitable for use herein are generally well-known in the art, and include, for example, (Z,Z,E)-3,6,8-dodecatrien-1-ol, and the aggregation pheromone n-hexanoic acid. The composition may also include one or more additional termite attractants such as food odor attractants or aggregation attractants. Without being limited thereto, suitable food odor attractants are described by Peterson (U.S. Pat. No. 5,756,114), the contents of which are incorporated by reference herein.

EXAMPLES

Having now generally described this invention, the same will be better understood by reference to certain specific examples, which are included herein only to further illustrate the invention and are not intended to limit the scope of the invention as defined by the claims.

Example 1

Collection of Termite Workers

Formosan subterranean termite workers, third instar or older based upon size, were obtained from bucket traps (Su and Scheffrahn. 1986. *Sociobiol.* 12: 299-304) set up at the Southern Regional Research Center, City Park, and the University of New Orleans, all of which are located in New Orleans, La. Formosan subterranean termite workers from four different colonies of termites were chosen to prevent colony vitality biasing of data.

Example 2

Collection and Identification of the Fungal Strains

In 2002, alates of *C. formosanus* were collected in universal black light traps (BioQuip, Gardena, Calif.) from several locations in New Orleans, La., between April and June, the normal swarming season. Termites were removed from the light traps within one hour, held overnight in plastic boxes containing moist paper towels, and brought to the laboratory the following morning. The alates from one particular collection in 2002 showed unusually high, rapid mortality; all alates died within 48 hours. Fungal mycelia and spores were visible on the cadavers. Several fungal strains isolated from the alate cadavers were purified individually.

Conidia were transferred from the dead alates onto potato dextrose agar (PDA) using sterile transfer loops. The plates were incubated at 25° C. for four to seven days until the mixed cultures sporulated. Fungal conidia were transferred to fresh PDA and incubated for an additional seven days at 25° C. The resulting colonies were repeatedly transferred onto fresh PDA as necessary until pure cultures were obtained. These pure cultures were incubated at 25° C. until sporulation was evident. Five morphologically different fungi were recovered using this isolation procedure.

To determine which strains were pathogenic to FST and whether these could be transferred from termite to termite, 10 workers were selected from each of the four colonies. The newly isolated strains could not immediately be tested on alates because the alate season had ended by the time the fungal strains had been purified. These termites were placed on the surface of a single heavily sporulating culture for 5 min, and then transferred to moistened filter paper in a Petri dish with ten of their uninoculated nestmates. The termites were incubated at 25° C. and 100% relative humidity. Of the five strains tested only one, designated C4-B, caused significant mortality among workers. By day 7, C4-B caused 63.8% mortality, whereas 100% of the termites were dead by the $14^{th}$ day (FIG. 1). The single strain, C4-B, that caused significant mortality was identified as *M. anisopliae* by Dr. Maren A. Klich (USDA/ARS, New. Orleans, La.) and placed into the Southern Regional Research Center Culture Collection as SRRC 2571.

Example 3

Mortality Assays

In 2003, effectiveness of C4-B was evaluated by exposing FST workers to either ESC 1, a strain of *M. anisopliae* produced commercially for control of termites under the product name BioBlast® or the newly identified strain C4-B. In initial experiments, the pathogenicity of strains C4-B and ESC 1 was compared by placing 20 FST workers from each of four colonies into a Petri dish (90×10 mm diameter) containing spores of strains C4-B or ESC 1, then incubating the termites on moistened filter paper.

Cultures of both C4-B and ESC 1 were grown for seven days at 25° C. on PDA. Spores were then harvested from the plates by scraping with a sterile spatula. An estimate of the number of spores was made using a hemacytometer (Hausser, Horsham, Pa.). A total of $6.5\times10^{10}$ spores of either C4-B or ESC 1 mixed with silica in a total volume of 1.5 g were individually distributed over the surface of moistened filter paper in Petri (90×10 mm diameter) dishes. The plates were incubated at 25° C., 100% RH. Mortality was recorded daily. Each treatment was replicated twice.

All (100%) of the workers in the C4-B-treated group were dead after 14 days; whereas, only 50% of the ESC 1—treated workers died during the same period (FIG. 2).

Example 4

Dose Response in Alates

Dilutions

To test efficiency of C4-B against alates, a dilution series of fungal spores in silica was applied to freshly collected alates. Groups of 20 alates were exposed as above to undiluted spores of each strain (C4-B and ESC 1), or to 1:10 or 1:100 dilutions of C4-B applied to each Petri dish. In a separate set of experiments, 1:10 and 1:100 serial dilutions of spores in silica resulted in the application of $9.7\times10^9$ and $9.7\times10^8$ per plate, respectively. Exposure to each of the C4-B treatments was replicated twelve times, whereas exposure to ESC 1 was replicated six times.

An undiluted dose of C4-B killed 100% of the exposed alates in 3 days whereas alates exposed to the 1:10 and 1:100 dilutions reached maximal mortality rates of 95.8% and 20.6° A) mortality by day 4, respectively (Table 1). By comparison, an undiluted preparation of strain ESC 1 caused a mortality rate of only 73.3% among alates after four days (Table 1).

TABLE 1

Percent mortality of *C. formosanus* alates caused by strains C4-B and Esc 1 of *M. anisopliae* during the 2003 swarming season.

| Isolate | Concentration | Days after treatment* | | | |
|---|---|---|---|---|---|
| | | 1 | 2 | 3 | 4 |
| Control | — | 7.9 ± 3.5 A | 19.4 ± 5.7 A | 29.7 ± 7.1 A | 43.8 ± 8.2 A |
| C4-B | undiluted | 22.9 ± 3.5 B | 90.6 ± 5.6 B | 100.0 ± 0.0 B | 100.0 ± 0.0 B |
| | 1:10 | 2.5 ± 1.4 A | 5.9 ± 2.5 C | 46.2 ± 7.6 C | 95.8 ± 3.7 B |
| | 1:100 | 0.8 ± 0.8 A | 2.1 ± 1.4 C | 4.6 ± 2.0 D | 20.6 ± 5.0 C |
| ESC 1 | undiluted | 21.7 ± 3.8 B | 55.0 ± 5.0 D | 65.8 ± 5.2 C | 73.3 ± 6.2 D |

*Values are Mean ± SE

Example 5

Spore Transmission Assays

Recently, Wright et al. (2002. *J. Appl. Entomol.* 126: 20-23) reported 50% mortality among FST workers, 5 to 6 days following exposure to ESC 1. Here, mortality of FST workers was examined when different proportions of termites were exposed to C4-B and incubated with uninfected nestmates. Of the 20 FST workers used in each replicate, members of a 0, 5, 10 or 20% subset were each inoculated with a 0.5 μl aliquot of a spore suspension containing $2 \times 10^6$ spores/μl. Termites were then transferred to Petri dishes containing moistened filter paper and the remaining nestmates. The plates were incubated at 25° C., 100% RH. Each treatment ratio was replicated three times. Individual colonies represented a single replicate in each experiment.

After 21 days, 5%, 10% and 20% ratios of infected to uninfected individuals caused mortality rates of 35.0%, 43.3% and 62.8%, respectively, compared to a control mortality rate of 14.5% (Table 2). Transmission of the C4-β isolate is evident by mortality of greater numbers of workers within 21 days than were originally exposed to spores of the fungus. Thus, with only 5% of the workers inoculated, 35% of the total population was killed by day 21 (Table 2). Transfer of a pathogen among termites, particularly in the case of subterranean termites, will be necessary for this fungus to work successfully as a biocontrol agent in the field.

TABLE 2

Transfer of *M. anisopliae* C4-B strain spores from inoculated to uninoculated *C. formosanus* workers*

| Percent of | Average percent mortality ± SD after days: | | |
|---|---|---|---|
| Infected termites | 7 | 14 | 21 |
| 0% (Control) | 3.3 ± 1.6 A | 7.8 ± 0.9 A | 14.5 ± 2.5 A |
| 5% | 11.2 ± 3.8 B | 21.7 ± 3.3 B | 35.0 ± 6.0 B |
| 10% | 18.9 ± 1.9 C | 30.0 ± 4.4 B | 44.3 ± 8.8 B |
| 20% | 33.3 ± 2.9 D | 42.8 ± 6.3 C | 62.8 ± 0.9 C |

*Values are Mean ± SE

Example 6

Dose Response in Alates

To determine the number of spores required to kill a single termite, dose response experiments were designed as a measure of mortality from a known inoculum. Alates were collected in May 2004 from light traps in New Orleans and were used the day after collection. Dilutions of C4-B spores were made in 0.05% Triton X-100 to final concentrations of $1 \times 10^0$ through $1 \times 10^6$ spores/μl. Spores were diluted in Triton X-100 to improve suspension of the spores and their adhesion to the surface of the termites. Alates were immobilized on ice, and a 1 μl aliquot of each spore suspension was applied to the ventral surface of each alate. Treated alates were left on ice for 20-30 min to allow the suspensions to dry on the surface of the insect. Groups of 5 alates were then transferred to (50×9 mm diameter) Petri dishes lined with moist filter paper and incubated at 28° C. and 100% RH. Control alates were treated with 1 μl of 0.05% Triton-X only. Each dilution and control was replicated three times. Mortality was recorded daily.

All alates exposed to a concentration of $10^6$ spores/μl were dead by three days after exposure, those exposed to $10^5$ and $10^4$ spores/μl, by 6 days, and those exposed to $10^3$ spores/μl, by nine days (FIG. 3). By the ninth day, treatments with $10^3$, $10^2$, $10^1$ and $10^0$ spores/μl had all reached a mortality rate of 93.3% (FIG. 3). The control mortality rate on Day 9 was 53.3%. The lower mortality rate of the controls in these experiments compared to the field trial controls is possibly due to the lower number of alates per Petri dish in these tests, which more closely matched the natural paired ratio of alates.

Example 7

Dose Response in Workers

The dose response experiment was repeated for FST workers with minor modifications from the alate dose response experiment. The termites were collected from three colonies using bucket traps (Su and Scheffrahn, 1998, supra). The spore concentrations used were $2 \times 10^1$ through $2 \times 10^6$ spores/μl and a dose of 0.5 μl was used per individual. The small size of the workers caused them to stick to the pipette tip as the spore suspension was being dispensed, so the delivery method was slightly modified. The suspension was instead dispensed as droplets onto a sheet of glass and a chilled, immobilized worker was placed dorsal side down onto each droplet. The workers remained on the glass plate for 20 min and were then transferred in groups of ten to (50×9 mm diameter) Petri dishes with moist filter paper and incubated as above. Control workers were treated with 0.5 μl of 0.05% Triton-X only. Dilution and control groups were replicated three times. Mortality was recorded daily.

Workers exposed to $10^6$ and $10^5$ spores/μl reached 100% mortality by day 6 (FIG. 4). No other treatment reached 100% mortality. The mortality in the control group was only 3.3% after six days (FIG. 4). Mortality caused by dilutions ranging from $10^4$ and $10^1$ spores/μl did not exceed 30% by day 12 of the experimental period (FIG. 4).

Example 8

Field Trial and Recovery of Fungi from Termite Cadavers

Field trials were performed to measure the effectiveness of strain C4-B against field-exposed alates. Two 2×2 m areas of turf set 57 m apart were selected near known swarming sites. The borders of the test areas were marked with flags. A black light (used in light traps) was placed in the center of each of the two areas. At the earliest indication of alate swarming, one of the areas was dusted with C4-B spores mixed with corn cob grits at a rate of $1 \times 10^{11}$ spores/m$^2$ in a total volume of 100 ml of corn cob grits. The other area was dusted with 100 ml of corn cob grits only.

After 20-30 min of alate activity around the lights, a 50×50 white cloth was placed on the ground in each area to attract the swarming alates from the grass. The alates crawled onto the white cloth. The pieces of cloth from the control and treated areas, with the alates attached, were transferred to plastic boxes. On the following morning 125 alates from each area were transferred in groups of 25 into 90×15 mm Petri dishes containing moist filter paper, and incubated at 28° C. and 100% RH. Mortality was recorded daily. The experiment was replicated once using alates collected from a different location.

Mortality of alates collected from the treated area reached 93.6% in three days while mortality of the untreated alates was only 34.0% on the same day (FIG. 5). Moreover, exposed alates showed 100% mortality in six days, while alates not exposed to the fungus showed a maximum of only 64.8% mortality on day 6 (FIG. 5). Groups of alates kept in Petri dishes do not generally survive longer than seven to eight days (data not shown). The relatively high mortality rate seen in FIG. 5 most likely reflects natural mortality of alates maintained in the laboratory. Captured alates generally experience high mortality unless they pair up and initiate a nuptial chamber (data not shown).

A 10% random sample of cadavers was selected for fungal recovery analysis. Individual alates were placed in separate sections of quadrant Petri dishes and were refrigerated until they could be analyzed, generally no more than overnight. Half of the cadavers were washed by being placed ventral side up on Whatman filter paper and saturated with 70% ethanol, which was allowed to dry. Alcohol washing removed and/or killed fungal spores on the surface of the termite to allow growth of fungi inside the cadaver. Both washed and unwashed cadavers were incubated in individual sections of quadrant PDA plates at 25° C. until growth was observed. Spores were serially transferred until a pure culture was obtained. The pure cultures were identified by Dr. Maren A. Klich (USDA/ARS, New Orleans, La.).

Recovery yielded more fungi from termites exposed to C4-B (78% from washed and 63% from unwashed cadavers) than controls (22% from washed and 37% from unwashed cadavers). Fungal cultures presumed to be *Metarhizium* sp. by morphological comparison to a representative sample were more evenly distributed with 45% recovered from washed C4-B, 23%, from unwashed C4-B, 25%, from washed control and 26%, from unwashed control cadavers (data not shown). It is not unusual to find *Metarhizium* spores on the surface of termites from natural exposure to the fungus in the soil. Further genetic analysis would be necessary to determine if the newly isolated virulent strain described here is the strain present in each of the cadavers. These data show that the majority of the fungi were recovered from the termites known to have been exposed to C4-B.

Statistical Analysis of Data: Data were analyzed using analysis of variance (ANOVA) and least significant difference (LSD) at $P \leq 0.05$ (Cody and Smith. 1997. In: Applied Statistics and the SAS Programming Language, Fourth Edition, Prentice-Hall, Inc., Upper Saddle River, N.J., pp. 150-180). In each experiment, treatments with the same letter on the same day are not significantly different. All analyses were run using the SAS System Software (Cody and Smith, 1997, supra).

*M. anisopliae*, strain C4-B, designated SRRC 2571, has been deposited with the U.S.D.A. Agricultural Research Service Patent Culture Collection (National Center for Agricultural Utilization Research, 1815 N. University Street, Peoria, Ill., 61604, on Mar. 6, 2006, under accession number NRRL 30905, as a patent deposit under the Budapest Treaty on the International Recognition of the Deposit of Microorganisms for the Purposes of Patent Procedure.

The subject cultures have been deposited under conditions that assure that access to the cultures will be available during the pendency of this patent application to one determined by the Commissioner of Patents and Trademarks to be entitled thereto under 37 CFR 1.14 and 35 USC 122. The deposits are available as required by foreign patent laws in countries wherein counterparts of the subject application, or its progeny, are filed. However, it should be understood that the availability of a deposit does not constitute a license to practice the subject invention in derogation of patent rights granted by governmental action.

Further, the subject culture deposits will be stored and made available to the public in accord with the provisions of the Budapest Treaty for the Deposit of Microorganisms, i.e., they will be stored with all the care necessary to keep them viable and uncontaminated for a period of at least five years after the most recent request for the furnishing of a sample of the deposit, and in any case, for a period of at least 30 (thirty) years after the date of deposit or for the enforceable life of any patent which may issue disclosing the cultures. The depositor acknowledges the duty to replace the deposits should the depository be unable to furnish a sample when requested, due to the condition of the deposit(s). All restrictions on the availability to the public of the subject culture deposits will be irrevocably removed upon the granting of a patent disclosing them.

All publications and patents mentioned in this specification are herein incorporated by reference to the same extent as if each individual publication or patent was specifically and individually indicated to be incorporated by reference.

The foregoing description and certain representative embodiments and details of the invention have been presented for purposes of illustration and description of the invention. It is not intended to be exhaustive or to limit the invention to the precise forms disclosed. It will be apparent to practitioners skilled in this art that modifications and variations may be made therein without departing from the scope of the invention.

We claim:

1. An isolated strain of *Metarhizium anisopliae* (*M. anisopliae*), strain C4-B (NRRL 30905), which is capable of increasing or enhancing mortality of Formosan and other subterranean termite workers and alates.

2. A biologically pure culture of *M. anisopliae* having the identifying characteristics of strain C4-B (NRRL 30905), wherein said identifying characteristics include the ability to increase or enhance mortality of both workers and alates of Formosan and other subterranean termites when said biologically pure culture is applied to the nest or populations of alates and/or workers.

3. A biocontrol agent comprising the biologically pure *M. anisopliae* strain of claim 1.

4. A biocontrol agent comprising the biologically pure *M. anisopliae* strain of claim 2.

5. A method for increasing or enhancing mortality of Formosan and other subterranean termite workers and alates comprising applying the biologically pure *M. anisopliae* strain of claim 1 or 2 to the nest or populations of alates and/or workers in an amount effective to increase or enhance mortality of said workers and alates, resulting in reduced populations of said workers and alates.

6. The method as claimed in claim 5, wherein the strain of *M. anisopliae* is applied to populations of alates and/or workers above ground.

7. A method as claimed in claim 5, wherein the strain of *M. anisopliae* is applied to populations of alates and/or workers below the soil surface.

8. A method as claimed in claim 5, wherein the strain of *M. anisopliae* is applied in a bait matrix.

9. A kit comprising a biocontrol agent of claim 3 or 4.

10. A fungal biocontrol composition comprising the biocontrol agent of claim 3 and a second biocontrol agent.

11. A fungal biocontrol composition comprising the biocontrol agent of claim 4 and a second biocontrol agent.

12. The biocontrol composition of claim 10 wherein the second biocontrol agent is a termiticide.

13. The biocontrol composition of claim 11 wherein the second biocontrol agent is a termiticide.

14. The biocontrol composition of claim 12 or 13 wherein the termiticide is selected from the group consisting of pathogenic nematodes, fungi, protozoans, viruses, bacteria, growth and developmental hormones and toxicants, chemical insecticides, and toxins derived from bacteria and fungi.

15. A fungal biocontrol composition comprising the biocontrol agent of claim 3 or 4 and further comprises insect attractants such as pheromones of the target termites or termite extracts containing pheromones or pheromone mimics.

16. A method for increasing or enhancing mortality of Formosan and other subterranean termite workers and alates comprising applying the biocontrol agent of claim 3 to the nest or populations of alates and/or workers in an amount effective to increase or enhance mortality of said workers and alates, resulting in reduced populations of said workers and alates.

17. A method for increasing or enhancing mortality of Formosan and other subterranean termite workers and alates comprising applying the biocontrol agent of claim 4 to the nest or populations of alates and/or workers in an amount effective to increase or enhance mortality of said workers and alates, resulting in reduced populations of said workers and alates.

18. The method as claimed in claims 16 or 17, wherein the biocontrol agent comprising a strain of *M. anisopliae* is applied to populations of alates and/or workers above ground.

19. A method as claimed in claims 16 or 17, wherein the biocontrol agent comprising a strain of *M. anisopliae* is applied to populations of alates and/or workers below the soil surface.

20. A method as claimed in claims 16 or 17, wherein the biocontrol agent comprising a strain of *M. anisopliae* is applied in a bait matrix.

21. The method of claim 16 or 17 further comprising applying a second biocontrol agent.

22. The method of claim 16 or 17 further comprising applying a second biocontrol composition wherein said second biocontrol composition is a termiticide.

23. The method of claim 16 or 17 further comprising applying insect attractants such as pheromones of the target termites or termite extracts containing pheromones or pheromone mimics.

* * * * *